United States Patent
Waki

(10) Patent No.: US 6,614,017 B2
(45) Date of Patent: Sep. 2, 2003

(54) LIQUID CHROMATOGRAPH MASS SPECTROMETER

(75) Inventor: Hiroaki Waki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 145 days.

(21) Appl. No.: 09/808,115

(22) Filed: Mar. 15, 2001

(65) Prior Publication Data

US 2001/0025923 A1 Oct. 4, 2001

(30) Foreign Application Priority Data

Mar. 23, 2000 (JP) ........................................ 2000-081575

(51) Int. Cl.[7] ................................................ H01J 49/06
(52) U.S. Cl. ...................................... 250/281; 250/288
(58) Field of Search ........................ 250/288; 204/452, 204/453

(56) References Cited

U.S. PATENT DOCUMENTS

| | | |
|---|---|---|
| 4,629,478 A | 12/1986 | Browner et al. |
| 5,171,990 A | 12/1992 | Mylchreest et al. |
| 5,581,081 A * | 12/1994 | Kato et al. .................. 250/288 |
| 5,753,910 A | 5/1998 | Gourley et al. |

OTHER PUBLICATIONS

WPI Accession No: 1999–235910 & JP110064288 A (Shimadzu).

* cited by examiner

*Primary Examiner*—John R. Lee
*Assistant Examiner*—Phillip A. Johnston
(74) *Attorney, Agent, or Firm*—Kanesaka & Takeuchi

(57) ABSTRACT

In a liquid chromatograph mass spectrometer, a solvent removing tube provided substantially horizontally between a spray chamber and a subsequent chamber is bent at an obtuse angle such that an entrance side of the tube is directed downwardly, and a nozzle is disposed such that a spraying direction of the nozzle is directed substantially downwardly and is approximately perpendicular to a central axis of the entrance side of the tube. Further, a drain for droplet or liquid is provided in front of the spraying direction of the nozzle. Since the spraying direction is oblique to a partition wall, the droplet or liquid sprayed from the nozzle collides against the drain, so that the droplet do not bounce to the entrance side of the solvent removing tube. Accordingly, the noise can be prevented, and the memory effect is also reduced in a high-density sample, so that an accurate analysis can be conducted.

5 Claims, 2 Drawing Sheets

LIQUID CHROMATOGRAPH MASS SPECTROMETER

BACKGROUND OF THE INVENTION AND RELATED ART STATEMENT

The present invention relates to a liquid chromatograph mass spectrometer (hereinafter referred to as LC/MS).

FIG. 2 is a schematic structural view showing one example of a general LC/MS. A liquid sample temporally separated and eluted from a column 11 of a liquid chromatograph (LC) section 10 is introduced into an interface section 20, and is sprayed in a spray chamber 22 from a nozzle 21 to be ionized. Generated ions pass through a solvent removing tube 23, such as a heated capillary, located in front of the nozzle 21, and the ions are sent to a mass spectrometer (MS) section 30.

The MS section 30 is formed of three chambers, that is, a first intermediate chamber 31, a second intermediate chamber 32 and an analysis chamber 33, wherein the aforementioned solvent removing tube 23 is provided between the spray chamber 22 and the first intermediate chamber 31, and a skimmer 35 having a through hole (orifice) with a very small diameter is formed between the first intermediate chamber 31 and the second intermediate chamber 32. An inside of the spray chamber 22 is maintained at an approximately atmospheric pressure, the first intermediate chamber 31 is exhausted to become an approximately 100 Pa by a rotary pump, and the second intermediate chamber 32 and the analysis chamber 33 are respectively exhausted by a turbo-molecular pump to become a range from approximately $10^{-1}$ Pa to $10^{-2}$ Pa and a range from approximately $10^{-3}$ to $10^{-4}$ Pa, respectively. That is, the vacuum conditions are gradually increased from the spray chamber 22 toward the analysis chamber 33.

Ions which have passed through the solvent removing tube 23 as described above are converged by deflector electrodes 34 into the orifice of the skimmer 35 such that the ions pass through the skimmer 35 and are introduced into the second intermediate chamber 32. Then, the ions are focused by ion lenses 36 and accelerated to be sent to the analysis chamber 33, and only objective ions having specific mass numbers (mass m/charge z) pass through a quadrupole filter 37 disposed in the analysis chamber 33 to thereby reach a detector 38. In the detector 38, an electric current in accordance with a number of the ions which have reached is taken out.

The interface section 20 is provided for generating gas ions by atomizing the liquid sample by heating, a high-speed air flow, a high electric field or the like, and an atmospheric pressure chemical ionization (APCI) method or an electrospray ionization (ESI) method has been used most widely. In the APCI method, a needle electrode is disposed in front of a distal end of the nozzle 21, and droplets of the liquid sample atomized by heating in the nozzle 21 are chemically reacted with carrier gas ions (buffer ions) generated by a corona discharge from the needle electrode, to conduct ionization. On the other hand, in the ESI method, a high voltage in the order of several kV is applied to the distal end of the nozzle 21, to thereby generate a strong non-uniform electric field. The liquid sample is subjected to a charge separation by this electric field, and the separated ions are pulled apart by a Coulomb attraction, so that the liquid sample is sprayed. By contacting the surrounding air, the solvent in the droplet is evaporated, and the gas ions are generated.

As shown in FIG. 3(a), a small droplet containing ions, which is generated by either the APCI method or ESI method described above, enters the solvent removing tube 23 due to momentum in case of being sprayed from the nozzle 21 and the aforementioned pressure difference between the spray chamber 22 and the first intermediate chamber 31. The solvent removing tube 23 is heated, and in the small droplet passing through the heated solvent removing tube 23, the evaporation of the solvent is accelerated by the heat. At the same time, as the size of the droplet is reduced, a voluntary destruction of the droplet due to Coulomb repulsion is further progressed, so that the droplet is ionized.

Ideally, the solvent in the small droplet sprayed from the nozzle 21 is supposed to be evaporated in the solvent removing tube 23 completely, and only ions proceed to the first chamber 31 and the subsequent sections to be subjected to the mass spectrometry. In reality, however, although a part of the small droplet is lessened, the liquid sample in the droplet condition proceeds to the first intermediate chamber 31, the skimmer 35 and so on, and enters the detector to generate a noise.

Therefore, in order to reduce the noise described above, various contrivances have been made to the solvent removing tube 23 and a positional relationship between the solvent removing tube 23 and the nozzle 21. Structures shown in FIG. 3(b) and FIG. 3(c) are respectively made such that the droplet is not directly sprayed toward the solvent removing tube 23. In FIG. 3(b), the nozzle 21 is disposed such that a spraying direction is oblique with respect to a central axis of the solvent removing tube 23, and in FIG. 3(c), the nozzle 21 is disposed such that the spraying direction is perpendicular to the central axis of the solvent removing tube 23. As described above, however, since the droplet is sucked or attracted not only by the momentum due to the spraying but also by the pressure difference between both chambers, those structures can not fully prevent the droplet from entering a subsequent chamber (first intermediate chamber 31).

Thus, as shown in FIG. 3(d), a system has been proposed, wherein a solvent removing tube 24 is bent at 90 degrees, and furthermore, the spraying direction of the nozzle 21 is directed perpendicular to a central axis of an entrance side of the solvent removing tube 24. According to this system, since the droplets entering the solvent removing tube 24 once collide against a tube wall of the de-solvent tube 24 at a bent portion, it is possible to greatly reduce a number of the droplets which advance straight and enter the subsequent chamber as they are.

In the structure as shown in FIG. 3(d), however, there were the following problems. Firstly, since the nozzle 21 is located at a position close to a partition wall 25 between the nozzle 21 and the subsequent chamber, the partition wall 25 is contaminated with the sample droplets sprayed from the nozzle 21. In the LC/MS in which the components of the sample change momentarily, contamination by the components at one point effects an analysis of the components at a next or subsequent point (so-called memory effect). This appears as a tail in the latter half of the component peak in a chromatograph, resulting in preventing an accurate analysis of the sample.

Also, since the partition wall 25 is contaminated, it has to be cleaned properly before an analysis for another sample. Further, since the spraying direction is perpendicular to the partition wall 25, the sprayed droplets collide against the partition wall 25, so that the droplets are gathered with the droplets nearby to grow into a larger droplet while the droplets are bouncing back. When the larger droplet described above reaches the entrance of the solvent removing tube 24 to be sucked, there is increased a possibility that the droplet does not evaporate in the solvent removing tube 24, and reaches the subsequent chamber.

The present invention has been made in order to solve the foregoing problems, and an object of the invention is to provide a liquid chromatograph mass spectrometer in which a noise is lowered and a memory effect is prevented in a high-density sample to thereby conduct an accurate analysis.

Further objects and advantages of the invention will be apparent from the following description of the invention.

SUMMARY OF THE INVENTION

To achieve the aforementioned object, the present invention provides a liquid chromatograph mass spectrometer, in which a solvent removing tube is disposed substantially horizontally between a spray chamber and a subsequent chamber, and the solvent removing tube includes an entrance side bent at an obtuse angle to be directed downwardly. Then, a nozzle is disposed in the liquid chromatograph mass spectrometer to have a spraying direction directed substantially downwardly and substantially perpendicularly to a central axis of the entrance side of the solvent removing tube, and a drain for droplets is disposed in front of the spraying direction of the nozzle.

Also, the liquid chromatograph mass spectrometer includes a partition wall between the spray chamber and the subsequent chamber, and the drain is disposed in the partition wall. Thus, even if the droplets sprayed from the nozzle collide against the drain in the partition wall, the droplets are discharged via the drain, so that the droplets do not return to the entrance side of the solvent removing tube. Accordingly, there can be reduced a possibility that the grown droplets enter the solvent removing tube. Also, since the exclusive drain is provided, the sample adhered on a wall surface of the drain can be washed away by water or solvent.

DETAILED DESCRIPTION OF PREFERRED EMBODIMENT

Figure 1:
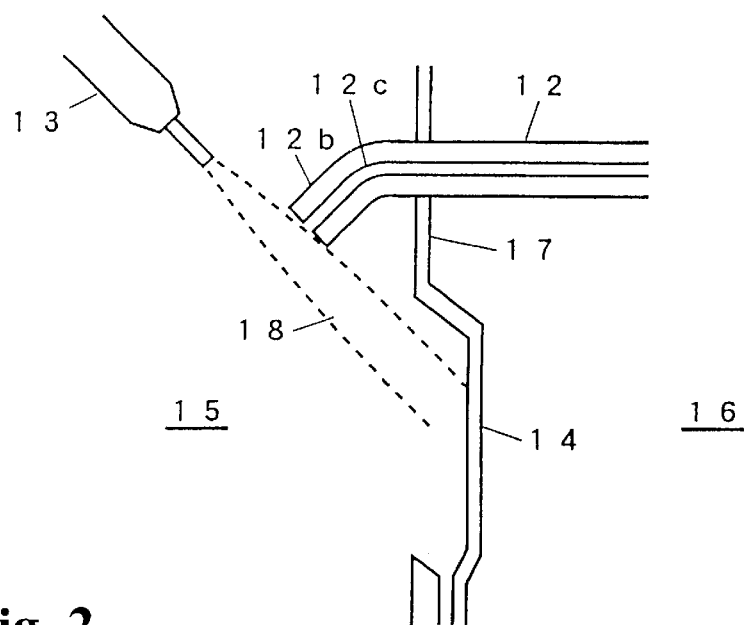
FIG. 1 is an explanatory view showing a structure of the invention.
Figure 2:
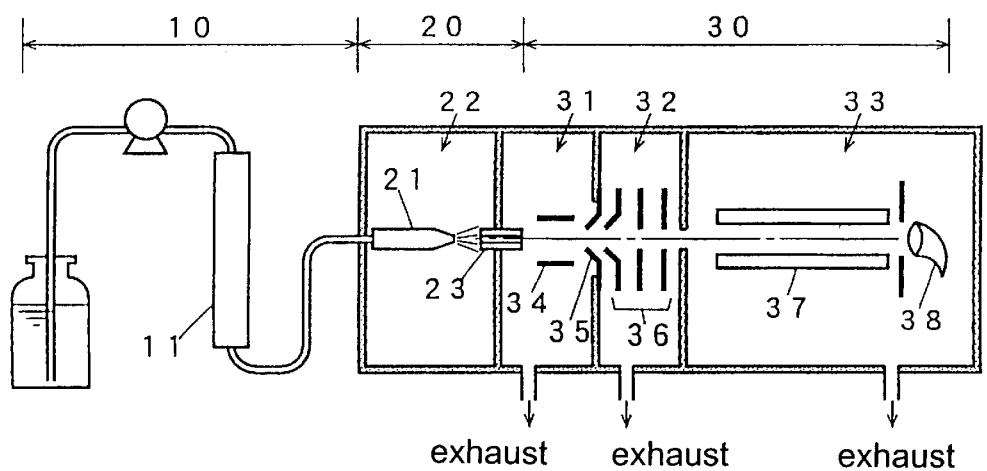
FIG. 2 is an explanatory view showing an entire structure of a conventional liquid chromatograph mass spectrometer.
Figure 3A:
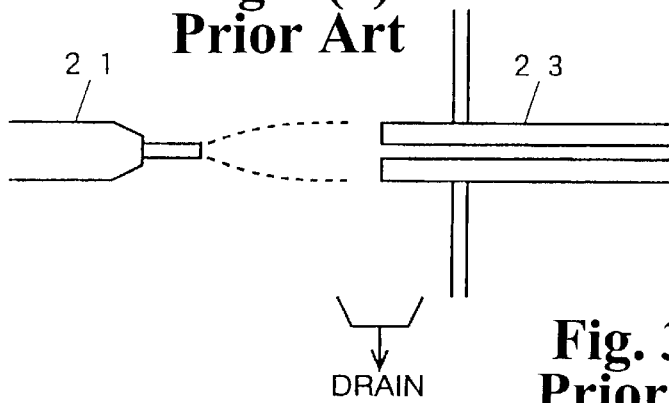
FIGS. 3(a) through 3(d) are explanatory views respectively showing positional relationships between a solvent removing tube and a nozzle in a conventional liquid chromatograph mass spectrometer.
Figure 3B:
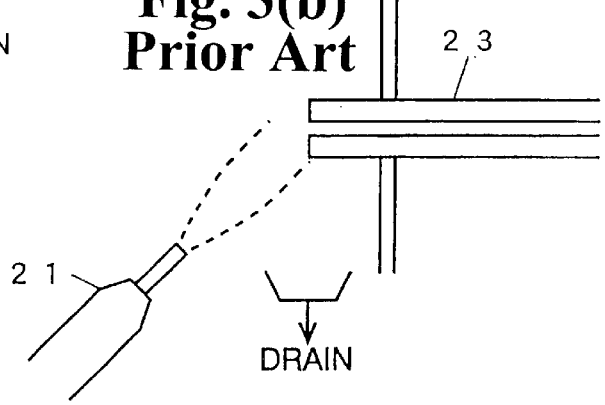
Figure 3C:
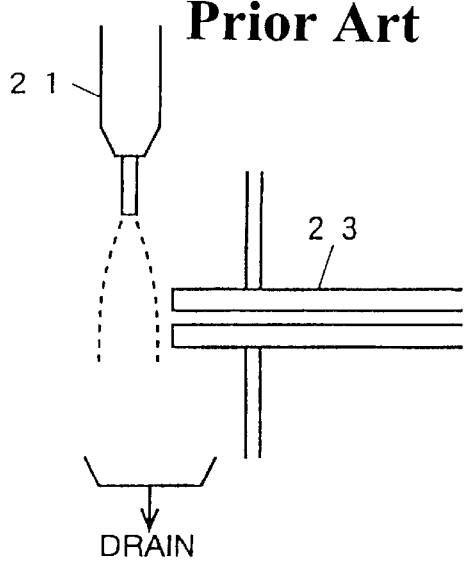
Figure 3D:
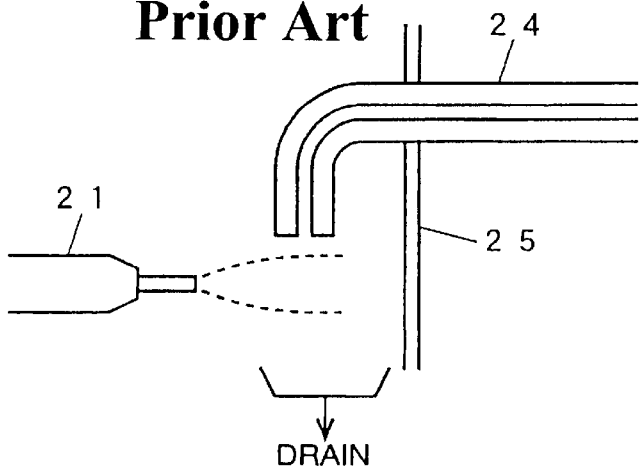

Hereinafter, an embodiment of the invention will be explained with reference to the attached drawings. In a liquid chromatograph mass spectrometer according to the present invention, a solvent removing tube 12, a nozzle 13 and a drain 14 are arranged substantially as shown in FIG. 1. In detail, the solvent removing tube 12 is disposed substantially horizontally to a partition wall 17 between a spray chamber 15 and a subsequent chamber 16 (first intermediate chamber 31 in FIG. 2), and an entrance side 12b (spray chamber 15 side) of the solvent removing tube 12 is bent slightly downwardly. A bending angle thereof is preferably in the order of 30 to 60 degrees. Incidentally, it is expressed as an obtuse angle when the solvent removing tube 12 is considered as a whole.

The nozzle 13 is disposed such that a spraying direction thereof is oriented substantially downwardly and substantially perpendicular to a central axis of the entrance side 12b of the solvent removing tube 12. Therefore, droplets 18 sprayed from the nozzle 13 do not plunge directly into the solvent removing tube 12 due to momentum thereof, and the droplets 18 are sucked by the solvent removing tube 12 only by a pressure difference between the spray chamber 15 and the subsequent chamber 16.

Also, since the spraying direction of the nozzle 13 is oblique to the partition wall 17, even if the sprayed droplets collide against a wall surface of a drain 14, the droplets do not return to the entrance side 12b of the solvent removing tube 12, resulting in greatly reducing a possibility that the grown droplet enters the solvent removing tube 12. Furthermore, since the solvent removing tube 12 is bent, even if the large droplet enters from the entrance side 12b, the droplet collides against an inner wall of the tube at a bent portion 12c, so that the droplet is prevented from directly entering the subsequent chamber 16. Accordingly, there can be greatly reduced a possibility that the large droplet proceeds to the subsequent chamber 16 and so on, and is detected by a detector to thereby generate a noise.

On the other hand, the droplets 18 which are sprayed from the nozzle 13 and are not sucked into the solvent removing tube 12 are collected by the drain 14 disposed at the partition wall 17 located in front of the spraying direction of the nozzle, and discharged to an outside of a system. Since the spraying direction of the nozzle 13 is slanted downwardly, the drain 14 can be disposed at a position away from the solvent removing tube 12, and accordingly, the memory effect described above can be reduced. Also, since the drain 14 is an exclusive drain, the sample adhered to the wall surface of the drain can be washed out by water, solvent or the like.

As described above, in the liquid chromatograph mass spectrometer according to the present invention, the droplets sprayed from the nozzle do not directly plunge into the solvent removing tube due to momentum thereof, and the droplets are sucked into the solvent removing tube only by the pressure difference between the spray chamber and the subsequent chamber. Also, since the spraying direction is slanted with respect to the partition wall, even if the sprayed droplets collide against the partition wall or drain, the droplets do not return to the entrance side of the solvent removing tube, resulting in greatly reducing a possibility that the grown droplet enters the solvent removing tube. Furthermore, since the solvent removing tube is bent, even if a large droplet enters from the entrance side, the droplet collides against the inner wall of the tube at the bent portion, so that the droplet is prevented from directly entering the subsequent chamber. Accordingly, the situation that the large droplet is detected by the detector by proceeding to the subsequent chambers to thereby generate a noise is greatly reduced.

Also, since the drain can be disposed at the position away from the solvent removing tube, the memory effect in the analysis can be reduced. Further, since the drain is the exclusive drain, the sample adhered to the wall surface of the drain can be easily cleaned by flowing water, solvent or the like.

Furthermore, since the nozzle is disposed obliquely, an entire length of the liquid chromatograph mass spectrometer, that is, a length in a direction from the nozzle to the detector, can be shortened, so that the entire apparatus can be made compact.

While the invention has been explained with reference to the specific embodiment of the invention, the explanation is illustrative and the invention is limited only by the appended claims.

What is claimed is:

1. A liquid chromatograph mass spectrometer, comprising:
   a spray chamber,
   a subsequent chamber disposed adjacent to the spray chamber,
   a partition wall situated between the spray chamber and the subsequent chamber,
   a solvent removing tube disposed substantially horizontally between the spray chamber and the subsequent chamber, said solvent removing tube having an entrance side bent at an obtuse angle to be directed downwardly,
   a nozzle disposed in the spray chamber and directed substantially downwardly toward the entrance side of the solvent removing tube, and
   a drain formed in the spray chamber disposed at the partition wall at a front side of a spraying direction of the nozzle, said drain being located obliquely relative to the spraying direction of the solvent removing tube.

2. A liquid chromatograph mass spectrometer according to claim 1, wherein said nozzle is disposed substantially perpendicularly to a central axis of the entrance side of the solvent removing tube.

3. A liquid chromatograph mass spectrometer according to claim 1, wherein said drain is dented toward the subsequent chamber to be spaced apart from the entrance side of the solvent removing tube.

4. A liquid chromatograph mass spectrometer according to claim 1, wherein said entrance side of the solvent removing tube is directed downwardly in a direction away from the partition wall and said nozzle is directed downwardly toward the partition wall crossing an area adjacent to a tip of the entrance side of the solvent removing tube.

5. A liquid chromatograph mass spectrometer according to claim 4, wherein said subsequent chamber has a pressure less than that in the spray chamber so that a material sprayed from the spray nozzle enters the solvent removing tube substantially by a sucking force due to a pressure difference between the spray chamber and the subsequent chamber.

* * * * *